United States Patent
Tolosa et al.

(10) Patent No.: US 9,486,641 B2
(45) Date of Patent: Nov. 8, 2016

(54) INCORPORATING AN OPTICAL WAVEGUIDE INTO A NEURAL INTERFACE

(71) Applicant: Lawrence Livermore National Security, LLC, Livermore, CA (US)

(72) Inventors: Vanessa Tolosa, Oakland, CA (US); Terri L. Delima, Livermore, CA (US); Sarah H. Felix, Oakland, CA (US); Satinderpall S. Pannu, Pleasanton, CA (US); Kedar G. Shah, San Francisco, CA (US); Heeral Sheth, Oakland, CA (US); Angela C. Tooker, Dublin, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 317 days.

(21) Appl. No.: 14/210,260

(22) Filed: Mar. 13, 2014

(65) Prior Publication Data
US 2014/0277296 A1    Sep. 18, 2014

Related U.S. Application Data

(60) Provisional application No. 61/802,409, filed on Mar. 16, 2013.

(51) Int. Cl.
*A61N 5/06* (2006.01)
*A61N 1/05* (2006.01)

(52) U.S. Cl.
CPC ......... *A61N 5/0601* (2013.01); *A61N 5/0622* (2013.01); *A61B 2090/571* (2016.02); *A61B 2562/12* (2013.01); *A61N 1/0529* (2013.01); *A61N 1/0551* (2013.01); *A61N 2005/063* (2013.01); *A61N 2005/0612* (2013.01); *Y10T 29/49204* (2015.01)

(58) Field of Classification Search
CPC .... A61N 5/06; A61N 5/0601; A61N 5/0622; A61N 2005/063; A61N 1/0529

USPC .............................. 606/2, 13–17; 607/88–92
See application file for complete search history.

(56) References Cited

U.S. PATENT DOCUMENTS

| | | | |
|---|---|---|---|
| 2005/0154435 A1* | 7/2005 | Stern | A61N 1/0529 607/116 |
| 2011/0087311 A1 | 4/2011 | Zorzos et al. | |
| 2011/0112591 A1 | 5/2011 | Seymour et al. | |
| 2012/0265184 A1* | 10/2012 | Sliwa | A61B 5/0084 606/15 |
| 2013/0030274 A1 | 1/2013 | Jamieson et al. | |
| 2013/0030352 A1 | 1/2013 | Seymour et al. | |

FOREIGN PATENT DOCUMENTS

WO    2013068696    6/2011

OTHER PUBLICATIONS

International Search Report and Written Opinion for PCT/US2014/030757 related to U.S. Appl. No. 14/210,260, 11 pages.

* cited by examiner

*Primary Examiner* — William Thomson
*Assistant Examiner* — John R Downey
(74) *Attorney, Agent, or Firm* — Eddie E. Scott

(57) ABSTRACT

An optical waveguide integrated into a multielectrode array (MEA) neural interface includes a device body, at least one electrode in the device body, at least one electrically conducting lead coupled to the at least one electrode, at least one optical channel in the device body, and waveguide material in the at least one optical channel. The fabrication of a neural interface device includes the steps of providing a device body, providing at least one electrode in the device body, providing at least one electrically conducting lead coupled to the at least one electrode, providing at least one optical channel in the device body, and providing a waveguide material in the at least one optical channel.

20 Claims, 3 Drawing Sheets

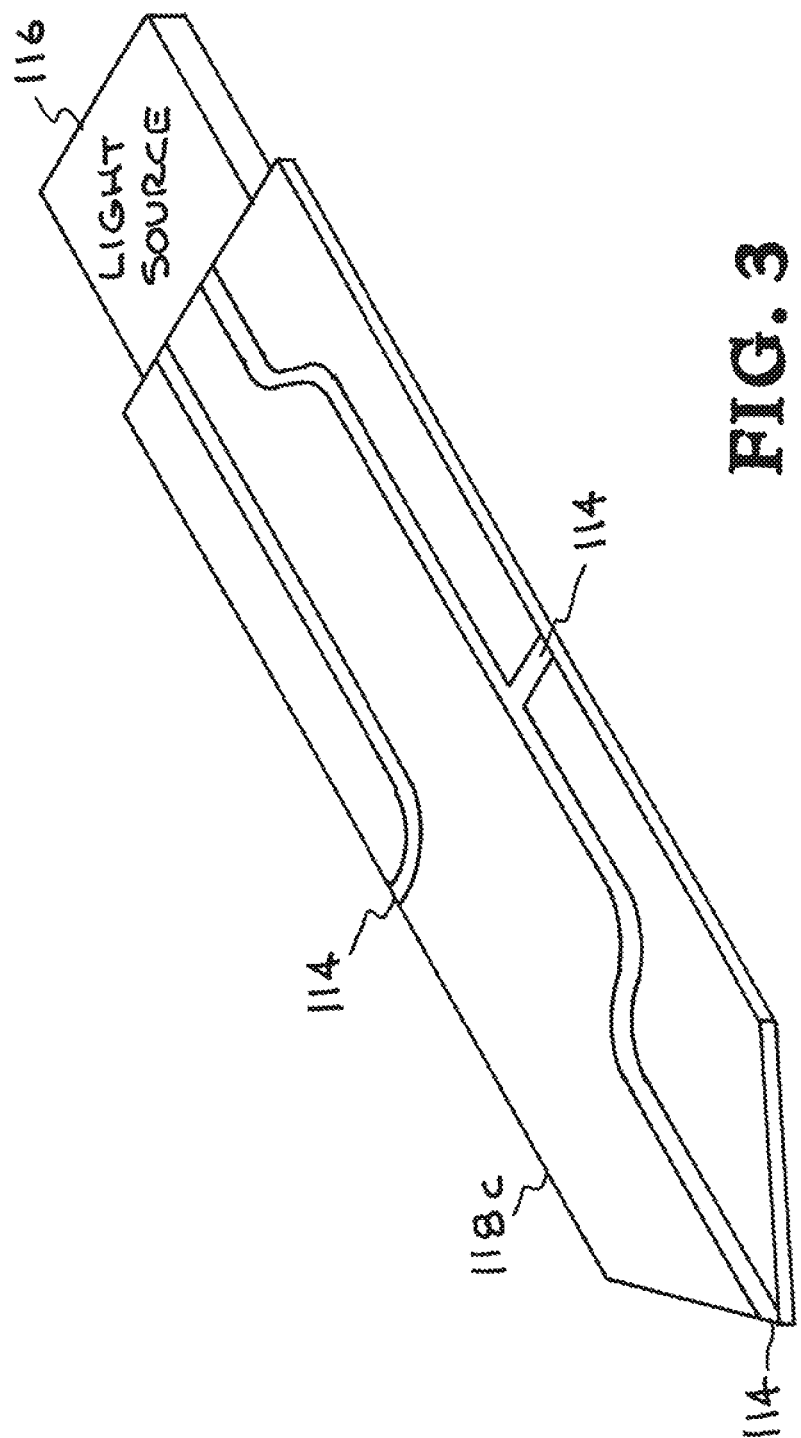

INCORPORATING AN OPTICAL WAVEGUIDE INTO A NEURAL INTERFACE

CROSS-REFERENCE TO RELATED APPLICATIONS

This application claims benefit under 35 U.S.C. §119(e) of U.S. Provisional Patent Application No. 61/802,409 filed Mar. 16, 2013 entitled "incorporating an optical waveguide into a neural interface," the disclosure of which is hereby incorporated by reference in its entirety for all purposes.

STATEMENT AS TO RIGHTS TO APPLICATIONS MADE UNDER FEDERALLY SPONSORED RESEARCH AND DEVELOPMENT

The United States Government has rights in, this application pursuant to Contract No. DE-AC52-07NA27344 between the United States Department of Energy and Lawrence Livermore National Security, LLC for the operation of Lawrence Livermore National Laboratory.

BACKGROUND

1. Field of Endeavor

The present application relates to microelectrode arrays and methods of fabrication, and particularly to incorporating an optical waveguide into a neural interface.

2. State of Technology

This section provides background information related to the present disclosure which is not necessarily prior art.

The current method to deliver light to light-sensitive cells in the brain and other parts of the nervous system is to use fiber optic waveguides. These fibers are commercially available and can be made as small as 50 um in diameter, however they are not ideal. At 50-200 um in diameter, the fibers are still too large to implant and study many important regions of the brain. Each fiber provides only one point of light source and one wavelength. There is a need for a light delivery system that is able to deliver multiple wavelengths as needed and in multiple areas, all with a minimal device footprint. To achieve this with fiber optics, 3 different fibers each at 50-200 um each would have to be implanted, and still this would only provide 3 light sources. Optical fibers also have low light delivery efficiency. Often a 100 mW source is required to deliver 1-5 mW to the desired site. The fiber optics is implanted separately and relatively far from the signal recording device. There is a need for a system wherein the recording electrodes are placed within microns of the delivered light source and the stimulated cells.

The current fiber optic waveguide system for delivering light to light-sensitive cells in the brain and other parts of the nervous system relies upon optical fibers that are too large to implant and study many important regions of the brain. The current fiber optic system is the only reliable method currently available, however it is not ideal. Each fiber is relatively large, can provide only one light source, one wavelength at time, and a high power loss by the time the light reaches its destination. In addition, the fiber is often implanted separately and relatively far from the signal recording device. Recording arrays with an attached fiber are made manually, leading to high variability and long labor time.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

Applicant's apparatus, systems, and methods provide an optical waveguide integrated into a multielectrode array (MEA) neural interface. Applicant's neural interface device includes a device body, at least one electrode in the device body, at least one electrically conducting lead coupled to the at least one electrode, at least one optical channel in the device body, and waveguide material in the at least one optical channel. Applicant's method of fabricating a neural interface device includes the steps of providing a device body, providing at least one electrode in the device body, providing at least one electrically conducting lead coupled to the at least one electrode, providing at least one optical channel in the device body, and providing a waveguide material in the at least one optical channel.

Applicant's apparatus, systems, and methods have use in the fabrication of implantable biomedical devices, specifically for optically interfacing with neurons and other excitable cells in such applications as optogenetics. Applicant's apparatus, systems, and methods can be applied to the manufacturing of any device requiring an incorporated lightguide. The incorporated lightguide can be used to deliver light in specific locations in the brain, spinal cord, or other tissue with light-sensitive proteins. The delivered light can be used to excited light-sensitive cells, e.g., specific neuronal cell types, while the multi-electrode array records electrical or chemical signals or while electrical stimulation is also delivered. By incorporating a lightguide into a multielectrode array implantable device, tissue and cells can be investigated electrically, chemically, and optically.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

FIG. 3 illustrates the integration of the waveguide material into the channels.

DETAILED DESCRIPTION OF SPECIFIC EMBODIMENTS

Figure 1:
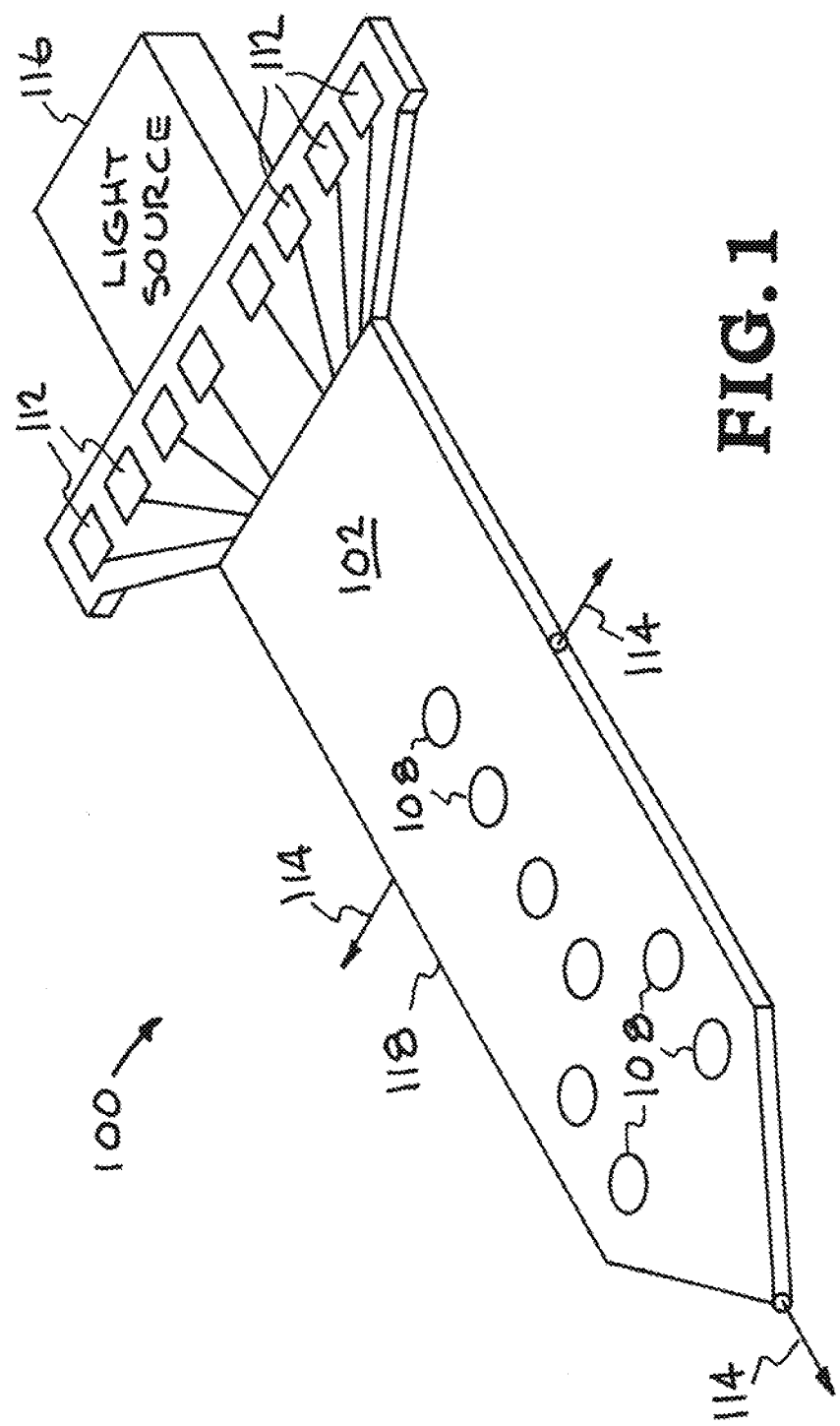
FIG. 1 is an illustration of a multielectrode array (MEA) with integrated optical waveguides.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

Applicant's apparatus, systems, and methods addresses the need for an integrated light guide that can deliver multiple wavelengths of light, in different locations, within microns of the recording array, and using a fabrication method that can be mass produced. Applicant's apparatus, systems, and methods utilize microtechnologies to fabricate waveguides integrated into a multielectrode array (MEA). In various embodiments the waveguides include a light conductive media in a reflective channel that is microfabricated via microelectromechanical systems (MEMS) technologies or direct ink writing. Applicant's apparatus, systems, and methods provide the fabrication of an optical waveguide integrated into a MEA neural interface. The waveguide material is made of light conducting material, e.g., air, water, saline, polymer, glass, encased in a channel with reflective or opaque walls to reduce loss of light.

Referring now to the drawings and in particular to FIG. 1, one embodiment of Applicant's multielectrode array (MEA) with integrated optical waveguides is illustrated. This embodiment of Applicant's multielectrode array (MEA) with integrated optical waveguides is designated generally by the reference numeral 100. As an overview, the device 100 has a body unit with two main operating components: (1) an electrode system, and (2) an optical waveguide system.

The device 100 is adapted to be implanted in the anatomy of a human or animal. A number of electrodes 108 are imbedded in the device 100 such that the electrodes 108 will be located in the desired position when the device 100 is implanted. The electrodes 108 are imbedded in a multi-layer body structure 102 as shown in FIG. 1. Lead wires or traces electrically couple the electrodes 108 to data collection and analysis equipment through contact pads 112. An optical waveguide system is contained in the multi-layer body structure 102. The optical waveguide system includes optical channels 114 and a light source/light detector 116. The body unit 102 has an electrically-insulating material construction enclosing lead wires or traces and the optical channels 114. The multi-layer body structure 102 is characterizable as an insulating polymeric body if insulating polymers are used or a flexible body if elastomeric insulating materials are used.

Figure 2:
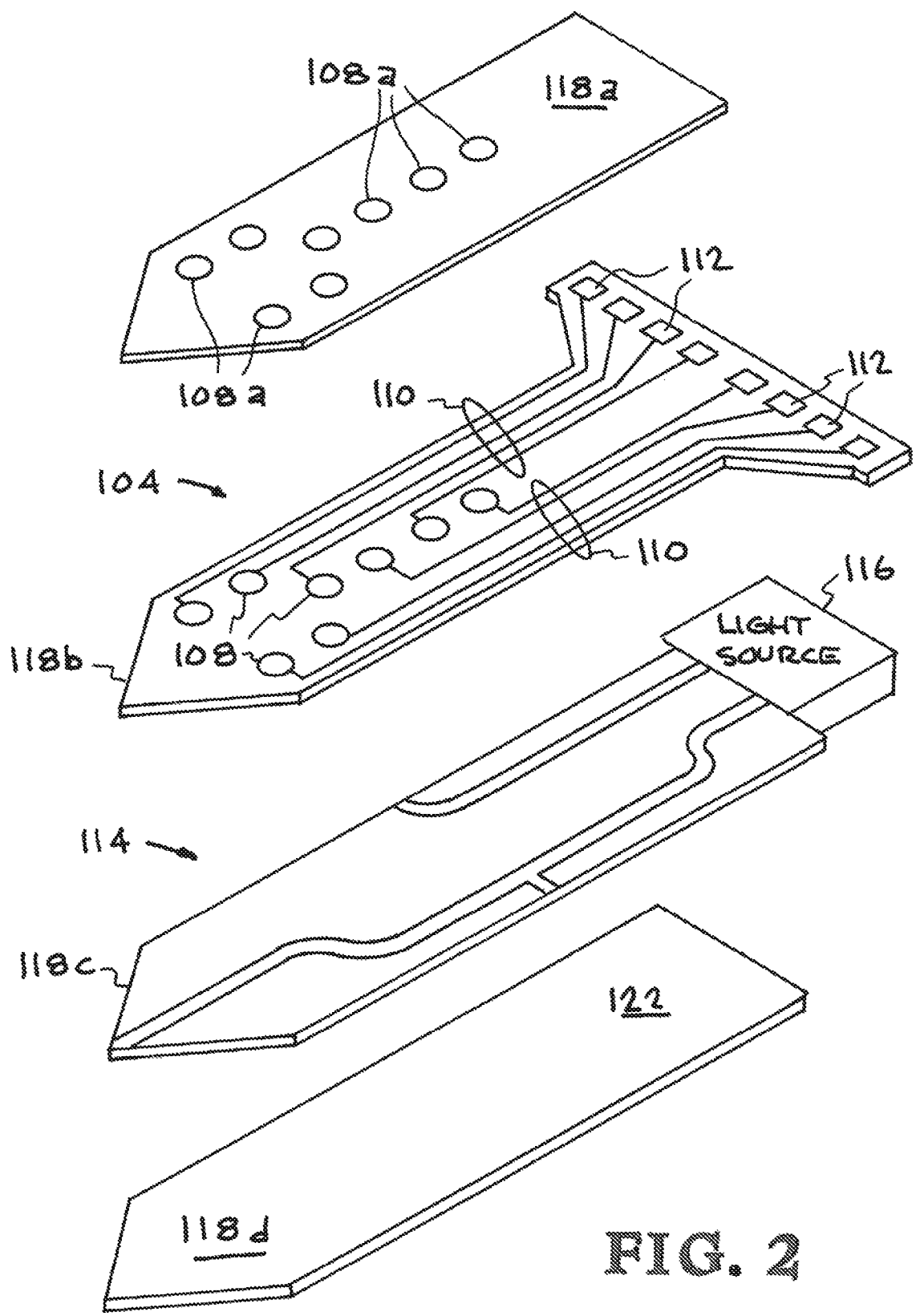
FIG. 2 illustrates the fabrication of the optical waveguide integrated into a MEA neural interface.

Referring now to FIG. 2, an exploded view of the device 104 is shown illustrating the fabrication of the optical waveguide integrated into a MEA neural interface. The top polymer layer 118a of the multilayer 118 body includes openings 108a for the electrodes 108. The second layer 118b of the multilayer 118 body includes the electrodes 108, the conductive lines 110, and the contacts 112. The third layer 118c of the multilayer 118 body includes the optical channels 114 and the light source/light detector 116. The fourth layer 118d of the multilayer 118 body is a polymer layer 122 that provides the bottom of the multilayer 118 body.

Applicant's apparatus, systems, and methods provide the fabrication of an optical waveguide integrated into a MEA neural interface. The waveguide material is made of light conducting material, e.g., air, water, saline, polymer, glass, encased in a channel with reflective or opaque walls to reduce loss of light. The optical waveguide system includes the optical channels 114 and the light source/light detector 116. The optical channels 114 are formed in the intermediate layer 118c of the multilayer body of the device.

Referring now to FIG. 3, the integration of the waveguide material is illustrated. Applicant's apparatus, systems, and methods provide the fabrication of an optical waveguide integrated into a MEA neural interface. The waveguide material is made of light conducting material, e.g., air, water, saline, polymer, glass, encased in a channel with reflective or opaque walls to reduce loss of light. The optical waveguide system includes the optical channels 114 and the light source/light detector 116. The optical channels 114 are formed in the intermediate layer 118c of the multilayer body of the device. The waveguide material is integrated in one of two ways:

The First Way—Incorporated into the microfabrication of the device using MEMS technologies to etch and deposit the light conductive material in the channel 114. In this method, the MEA substrate 118c can be silicon-based or polymer-based (eg., parylene, polyimide). Each channel can be 5-100+ um in diameter depending on the application. Hollow channels 114 for the light conductive material can be fabricated into an already reflective substrate (e.g, silicon) or a reflective material can be used to coat the inner walls of the channel 114. The reflective material can be deposited using a highly conformal deposition method like atomic layer deposition or other vapor deposition methods. To provide multiple light sources, the channel walls can be etched away along the length of the guide. To provide multiple light sources or wavelengths, several channels with light conductive material, could be fabricated into a single MEA.

The Second Way—Incorporated into the MEA by depositing the light conductive material and channel material using direct ink writing. In this method, a dual concentric ink nozzle will be used to deposit the light conductive material and the channel wall material at the same time. Multiple waveguide channels can be deposited on a single MEA. Each channel can be 5-100+ um in diameter depending on the application. To provide multiple light sources, the channel walls can be etched away in specific regions along the guide or lapses in deposition of the channel wall (outer nozzle) can be programmed into the deposition pattern. To provide different light sources or wavelengths simultaneously, multiple waveguides can be deposited on the MEA.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described, and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The invention claimed is:

1. A method of fabricating a neural interface device, comprising the steps of:
   providing a multilayer device body having a first polymer layer with at least one opening,
   providing at least one electrode in said at least one opening in said first polymer layer of said device body,
   providing a second polymer layer of said multilayer device body that includes at least one electrically conducting lead coupled to said at least one electrode,
   providing a third polymer layer of said multilayer device body that includes at least one optical channel,
   providing a waveguide material in said at least one optical channel, and
   providing a fourth polymer layer,
   wherein said first polymer layer, said second polymer layer, said third polymer layer, and said fourth polymer layer are in a stacked relationship to each other and said first polymer layer provides a top of said multilayer device body and said fourth polymer layer provides a bottom of said multilayer device body.

2. The method of fabricating a neural interface device of claim 1 further comprising providing at least one electrical contact connected to said at least one electrically conducting lead.

3. The method of fabricating a neural interface device of claim 1 wherein said step of providing a multilayer device body comprises providing a multilayer polymer-based device body.

4. The method of fabricating a neural interface device of claim 1 wherein said step of providing a waveguide material in said at least one optical channel comprises providing a light conductive media in said at least one optical channel.

5. The method of fabricating a neural interface device of claim 1 wherein said step of providing a waveguide material in said at least one optical channel comprises providing a light conductive glass in said at least one optical channel.

6. The method of fabricating a neural interface device of claim 1 wherein said step of providing a waveguide material in said at least one optical channel comprises providing a light conductive polymer in said at least one optical channel.

7. The method of fabricating a neural interface device of claim 1 wherein said step of providing a waveguide material in said at least one optical channel comprises providing a light conductive water in said at least one optical channel.

8. The method of fabricating a neural interface device of claim 1 wherein said step of providing a waveguide material in said at least one optical channel comprises providing light conductive ink in said at least one optical channel.

9. The method of fabricating a neural interface device of claim 1 wherein said step of providing a waveguide material in said at least one optical channel comprises providing a light conductive saline solution in said at least one optical channel.

10. The method of fabricating a neural interface device of claim 1 wherein said step of providing at least one optical channel in said multilayer device body comprises providing at least one optical channel having light reflective walls.

11. The method of fabricating a neural interface device of claim 1 wherein said step of providing at least one optical channel in said multilayer device body comprises providing at least one optical channel having opaque walls.

12. A neural interface device having a multilayer device body, at least one electrode in said device body, at least one electrically conducting lead coupled to said at least one electrode, at least one optical channel in said device body, and waveguide material in said at least one optical channel produced by the process comprising the steps of:
   providing a multilayer device body having a first polymer layer with at least one opening,
   providing at least one electrode in said at least one opening in said first polymer layer of said device body,
   providing a second polymer layer of said multilayer device body that includes at least one electrically conducting lead coupled to said at least one electrode,
   providing a third polymer layer of said multilayer device body that includes at least one optical channel,
   providing a waveguide material in said at least one optical channel, and
   providing a fourth polymer layer,
   wherein said first polymer layer, said second polymer layer, said third polymer layer, and said fourth polymer layer are in a stacked relationship to each other and said first polymer layer provides a top of said multilayer device body and said fourth polymer layer provides a bottom of said multilayer device body.

13. The neural interface device of claim 12 wherein said waveguide material is a light conductive media.

14. The neural interface device of claim 12 wherein said waveguide material is a light conductive media and wherein said at least one optical channel is a reflective channel.

15. The neural interface device of claim 12 wherein said at least one optical channel has walls that are reflective.

16. The neural interface device of claim 12 wherein said at least one optical channel has walls that are opaque.

17. The neural interface device of claim 12 wherein said waveguide material is glass.

18. The neural interface device of claim 12 wherein said waveguide material is a polymer.

19. The neural interface device of claim 12 wherein said waveguide material is saline.

20. The neural interface device of claim 12 wherein said waveguide material is water.

* * * * *